United States Patent
Babler

[19]

[11] Patent Number: 6,113,265
[45] Date of Patent: Sep. 5, 2000

[54] C-ARM APPARATUS WITH IMPROVED C-ARM LOCKING MECHANISM

[75] Inventor: Egon S. Babler, Northbrook, Ill.

[73] Assignee: Fluorscan Imaging Systems, Inc., Northbrook, Ill.

[21] Appl. No.: 09/199,952

[22] Filed: Nov. 24, 1998

Related U.S. Application Data

[60] Provisional application No. 60/066,966, Nov. 28, 1997.

[51] Int. Cl.$^7$ ........................................... H05G 1/02
[52] U.S. Cl. ............................... 378/197; 378/198
[58] Field of Search ..................... 378/195–198

[56] References Cited

U.S. PATENT DOCUMENTS 4,209,706  6/1980  Nunan .

Primary Examiner—Craig E. Church
Attorney, Agent, or Firm—Cooper & Dunham LLP

[57] ABSTRACT

In a mini C-arm x-ray imaging system in which an x-ray source and detector are mounted at opposite ends of a C-shaped track which is supported for sliding orbital movement along its axis of curvature for positioning the source and detector in relation to an object to be imaged, a locking mechanism including a brake shoe bearing against the track, a screw and nut carried by the track-supporting structure for moving the shoe toward and away from the track, a resilient bias acting between the shoe and the screw to urge the shoe toward the track, a handle for turning the screw to move the shoe, and a detent acting between the handle and the support structure to provide a plurality of discrete settings for the handle, respectively representing incrementally different forces exerted by the shoe against the track.

9 Claims, 7 Drawing Sheets

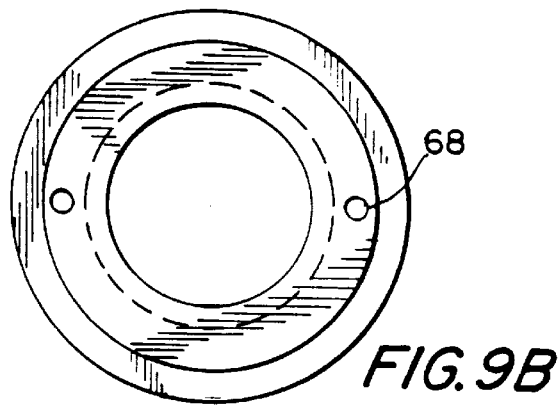
*FIG. 9B*
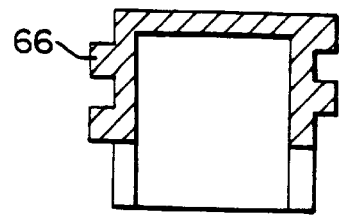
*FIG. 10A*
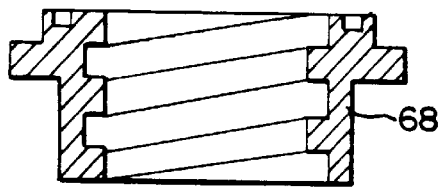
*FIG. 9A*
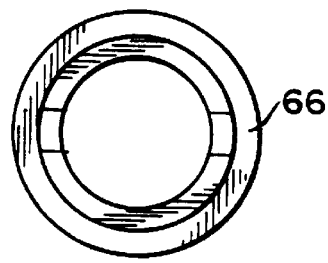
*FIG. 10B*
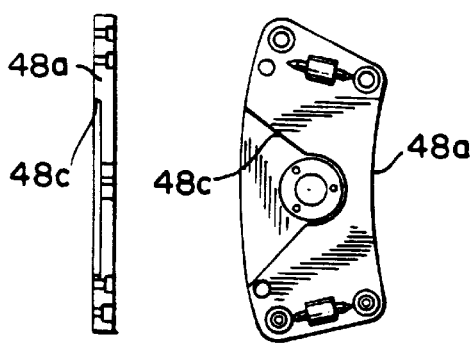
*FIG. 11B*  *FIG. 11A*
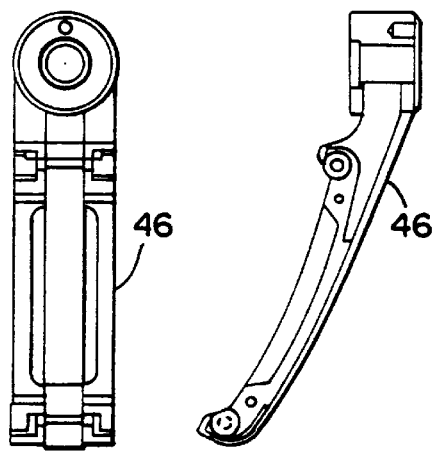
*FIG. 12B*  *FIG. 12A*

C-ARM APPARATUS WITH IMPROVED C-ARM LOCKING MECHANISM

CROSS-REFERENCE TO RELATED APPLICATION

This application is a continuation-in-part of applicant's U.S. provisional patent application Ser. No. 60/066,966, filed Nov. 28, 1997, the entire disclosure of which is incorporated herein by this reference.

BACKGROUND OF THE INVENTION

This invention relates to C-arm apparatus and, in an important aspect, to mini C-arm systems such as are used for fluoroscopic imaging of a human patient's extremities and for other medical diagnostic purposes. More particularly, the invention relates to mini C-arm imaging apparatus incorporating new and improved locking mechanisms for holding the C-arm stationary in a selected position relative to C-arm supporting structure.

Mini C-arm imaging systems are well known and widely used in present-day medical practice, e.g. to provide fluoroscopic images and/or bone mineral density measurements of a human patient's extremity such as a wrist, hand, ankle or foot. One example of such mini C-arm apparatus is described in copending allowed U.S. patent application Ser. No. 08/794,615 filed Feb. 3, 1997 (in which the issue fee has been paid), the entire disclosure of which is incorporated herein by this reference. Another example is the apparatus described in U.S. Pat. No. 5,627,873, the entire disclosure of which is also incorporated herein by this reference.

As set forth in the allowed application and patent just cited, a mini C-arm system of the type herein contemplated includes a rigid C-shaped track continuously curved along an arc of a circle, with two opposed ends spaced apart by a gap and respectively carrying an x-ray source and an x-ray detector that face each other across the gap so that x-rays emitted by the source are incident on and detected by the detector. The source and detector are so arranged that when an object such as a human extremity is interposed in the gap and irradiated with x-rays from the source, the detector produces data representative of characteristics of the interposed object. The produced data, by way of illustration, may be displayed on a CRT as a fluoroscopic image of the object, or may be used (as the aforementioned allowed application Ser. No. 08/794,615 describes) to measure bone mineral density (BMD) of bone in the extremity.

The C-arm track is slidably mounted in a support member so as to be movable, relative to the support member, along a circular path substantially coincident (i.e. concentric) with the arc of curvature of the track. By such sliding movement, the x-ray source and detector can be moved rotatably about the center of circular curvature of the C-arm track. The support member, in turn, is pivoted on the distal end of an arm (or, preferably, an articulated arm assembly including two or more sections movable relative to each other) having a proximal end pivotally secured to a base. The pivotal interconnections between the support member, arm or articulated arm assembly, and base, together with the provision of sliding rotary movement of the C-arm relative to the support member, afford a plurality of modes of movement of the source and detector, including rotation about various differently-oriented axes, as desired to enable optimum positioning of the x-ray source and detector in relation to an object such as a patient extremity which is to be imaged and/or otherwise examined with the mini C-arm device.

Advantageously the various interconnections, pivots and articulations permit relatively easy movement, to facilitate positioning of the source and detector by a user such as a physician. Once the source and detector have been moved to a selected location and orientation, however, it is important that they be held fixed in position for the duration of irradiation of the patient. To this end, and again as shown in the aforementioned application and patent, it is known to provide means manipulable by the user for releasably locking the C-arm in relation to the support member and for releasably locking the pivotal joints. As the aforementioned patent also describes, the mini C-arm track, with its source and detector, may be mass balanced about the center of curvature of the track to aid in stabilizing the C-arm at any desired position relative to the support member, although this mass balancing does not obviate the provision of locking means. Locking means heretofore used to hold the C-arm track fixed in relation to the support member have typically been screw mechanisms carried by the support member for bearing frictionally, when tightened, against a surface of the curved track.

In use of a mini C-arm x-ray system to image or otherwise examine a patient's extremity, it is customary to place a surgical drape around the source and detector and the patient's extremity to maintain sterility during the examining procedure. When the C-arm or the entire support mechanism is rotated during positioning, the drape may accidentally catch and pull on the locking mechanism, loosening it sufficiently to permit the C-arm track to slide relative to the support arm. Such dislodgment of the C-arm track, source and detector from a preset position relative to the support member (e.g., during adjustment of one or another of the pivoted joints associated with the articulated arm assembly) is highly undesirable, causing inconvenience and loss of time.

Moreover, physicians using a mini C-arm system often want to employ the locking mechanism to apply light friction or drag on the C-arm track during the positioning phase of an examining procedure, so that the track will remain in a tentatively selected position but can be slidably displaced (relative to the support member) by manually applied force at a later stage in the positioning phase. With a conventional screw-type locking mechanism, it is difficult to manually fine-tune the tightening of the screw so as to provide such light drag.

SUMMARY OF THE INVENTION

An object of the invention is to provide, in C-arm apparatus such as the mini C-arm x-ray systems discussed above, new and improved mechanism for locking the C-arm track in a selected position of its orbital rotation about its center of curvature relative to a supporting member in which the track slides. Further, specific objects are to provide such a mechanism affording a plurality of different, easily settable degrees of drag on the track, and to provide such a mechanism having improved security against accidental dislodgment as by the pulling force of a moving surgical drape.

The present invention is embodied in C-arm apparatus including a rigid C-shaped track having a circular arc of curvature and opposed free ends, spaced apart by a gap, for respectively bearing two elements which are to be maintained in fixed relation to each other and to be adjustably positionable in relation to an object which is to be disposed in the gap, the track having a surface extending along its length; and a member supporting the track for longitudinal guided sliding movement along an arcuate path coincident with the arc of curvature of the track to orbit the elements. To the foregoing and other ends, the invention broadly contemplates the provision, in such apparatus, of locking mechanism comprising, in combination, a brake shoe for bearing against the track surface; a driver, mounted in the supporting member and carrying the brake shoe, for moving the brake shoe toward and away from the track surface through a range of positions between a first position in which the shoe bears against the track surface with full braking force to prevent movement of the track along the path and a second position in which the shoe exerts substantially no braking force on the surface, the shoe being resiliently compressible toward the driver so that as the shoe moves progressively through at least a substantial part of its range of positions, it exerts a progressively varying force on the track surface; a handle connected to the driver for operating the driver to move the shoe through the aforesaid range of positions; and a detent cooperating with the handle to releasably arrest the handle in each of a plurality, greater than two, of locations respectively corresponding to a like plurality of positions of the shoe, within the range of shoe positions, including the first and second positions.

Further in accordance with the invention, in convenient and currently preferred embodiments thereof, the apparatus includes a resilient bias-exerting device (e.g. a spring) acting between the shoe and the driver so that the shoe is resiliently compressible toward the driver as aforesaid, the bias exerted by this device urging the shoe away from the driver to a limited extent such that when the shoe is in the second position it does not engage the track surface.

Advantageously the driver comprises a screw connected to the brake shoe and a nut carried by the supporting member, the screw being threaded in the nut whereby the screw and nut have a common thread axis, the handle being connected to one of the screw and nut for rotation therewith about the thread axis, and the other of the screw and nut being held against rotation about the thread axis. Thus, the handle may be keyed to the screw so that the screw and handle rotate together while the screw has a limited range of axial movement relative to the handle, and the nut may be fixedly mounted in the supporting member.

In particular embodiments of the invention, the handle has a surface, facing a portion of the supporting member, formed with a plurality of indentations corresponding in number to the aforesaid plurality of handle locations, and the detent comprises a spring-loaded body having a convexly rounded surface, mounted in the last-mentioned portion of the supporting member so as to be sequentially receivable in the handle indentations to arrest the handle at each of the plurality of locations.

Also, the screw may be formed with a central cylindrical recess having a geometric axis and an open end facing the track surface, the brake shoe being received within the recess and axially movable therein; and a resiliently compressible spring may be disposed within the recess to act between the screw and the brake shoe, urging the brake shoe toward the track surface.

In at least many instances it is desirable to apply simultaneous braking forces against opposed longitudinal surfaces of the C-shaped track, i.e., with two opposed brake shoes effectively clamping the track between them. Thus, where the track has a second surface extending along its length and opposed to the first-mentioned surface, the locking mechanism may include a second brake shoe for bearing against that second surface, and a second driver, mounted in the supporting member and carrying the second brake shoe, for moving the second brake shoe toward and away from the second track surface through the aforesaid range of positions, the second shoe being resiliently compressible toward the second driver such that as the second shoe moves progressively through at least a substantial part of its range it exerts a progressively varying force on the second track surface, the handle being connected to the second driver (as well as to the first driver) for operating the second driver to move the second brake shoe through the range of positions as the first shoe moves through the range of positions, the first and second shoes cooperating to exert braking force simultaneously against both the first-mentioned surface and the second surface of the track.

In C-arm x-ray systems embodying the invention, the two elements carried by the track are, respectively, an x-ray source and an x-ray detector that face each other across the gap so that x-rays emitted by the source are incident on and detected by the detector, the source and detector being so arranged that when an object such as a human extremity is interposed in the gap and irradiated with x-rays from the source, the detector produces data representative of characteristics of the interposed object.

More particularly, the invention contemplates the provision of the foregoing features, including the described locking mechanism, in a mini C-arm fluoroscopic imaging system, which includes an arm assembly having a proximal end and a distal end, the supporting member being pivotally mounted on the distal end of the assembly for rotation relative thereto about a first axis; and a base to which the proximal end of the arm assembly is pivotally mounted for rotation about a second axis different from the first axis.

The present invention achieves the aforementioned objects, in particular, through the combination of the resilient bias or resilient compressibility of the mounting of the brake shoe or shoes and the multiple-setting detent mechanism wherein the different settings correspond to respectively different positions of the shoe or shoes. That is to say, owing to the resilient bias, such different shoe positions respectively provide incrementally different forces exerted by the shoe against the track, enabling the physician operating the C-arm equipment to readily select a desired degree of drag simply by moving the handle to the appropriate detent setting. Such a procedure is easier and more certain than attempting to adjust the degree of force exerted by a simple, continuously turnable screw-type braking mechanism. The detent also resists dislodgement of the brake shoe more surely than a simple screw-type mechanism, especially in situations where the screw has been delicately manipulated to some light or intermediate-drag position.

Further features and advantages of the invention will be apparent from the detailed description hereinbelow set forth, together with the accompanying drawings.

BRIEF DESCRIPTION OF THE DRAWINGS

FIGS. 9A and 9B are, respectively, sectional elevational and plan views of the driver nut in the locking mechanism of FIG. 6;

FIGS. 10A and 10B are, respectively, elevational sectional and plan views of the driver screw in the locking mechanism of FIG. 6;

FIGS. 11A and 11B are, respectively, side and front elevational views of a side plate of the guide structure of the supporting member in the embodiment of FIG. 4; and FIGS. 12A and 12B are, respectively, side and front elevational views of the main body of the supporting member in the embodiment of FIG. 4.

DETAILED DESCRIPTION

Figure 1:
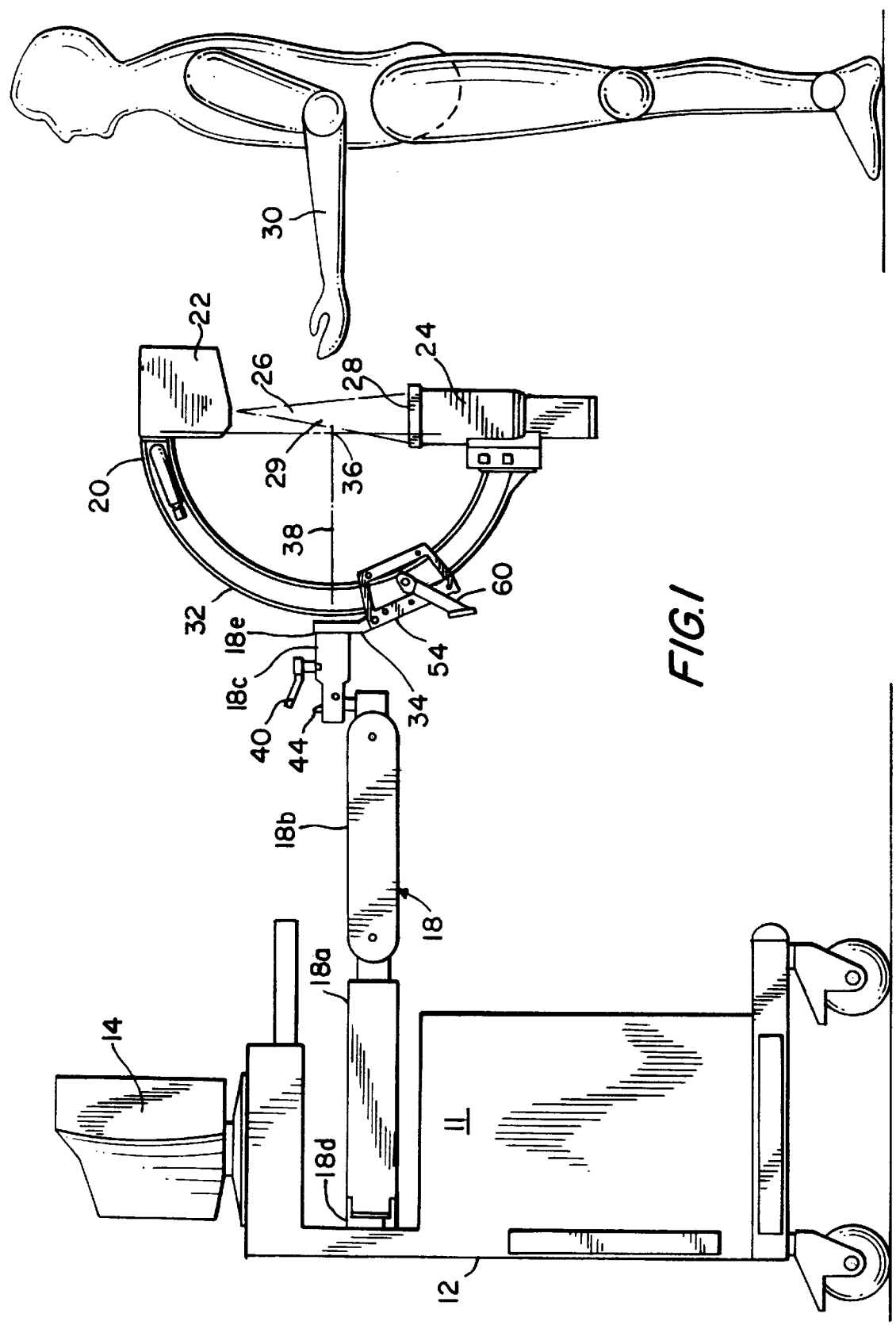
FIG. 1 is a simplified and partly schematic side elevational view of mini C-arm x-ray fluoroscopic imaging apparatus incorporating an illustrative embodiment of the present invention.

The invention will be described, with reference to the drawings, as embodied in a mini C-arm x-ray fluoroscopic imaging system 10 (FIG. 1) which is entirely contained in a wheeled cart or cabinet 11 that can easily be rolled from place to place. The cabinet includes a generally rectangular, upright body 12 that supports one or dual video monitors 14 (only one being shown) on its top surface and has, in its upper portion, an articulated arm assembly 18; the cabinet also contains a computer (not shown) for processing data.

The outer end of the articulated arm assembly 18 carries a mini C-arm 20 having an x-ray source 22 and a detector 24 respectively fixedly mounted at its opposite extremities so that an x-ray beam 26 from source 22 impinges on the input end 28 of the detector, the source and detector being spaced apart by the C-arm sufficiently to define a gap 29 between them, in which the limb or extremity of a human patient 30 can be inserted in the path of the x-ray beam 26. The mounting of the C-arm and associated portion of assembly 18, as hereinafter further described, is such as to enable the C-arm to be swivelled or rotated about each of three different axes and to be held stably at any desired position, while the arm assembly 18 is itself mounted and jointed to enable its outer end and the C-arm to be angularly displaced both horizontally and vertically. The multidirectional angular movability of the mini C-arm facilitates the positioning of the source and detector in relation to a patient body portion to be irradiated.

A suitable power supply and operating controls for the x-ray source, with instrumentalities for controlling or varying current and voltage, not shown, are incorporated in the system as well.

The beam 26 emitted by the x-ray source 22 is a cone-shaped beam that impinges on a flat x-ray-sensitive receiving surface of the detector 24 at or adjacent to the detector input end; the detector, which may be of a known type, produces output data signals including, for example, image data with respect to a patient's extremity interposed between the source and detector. The output data from the detector are transmitted to and processed by the onboard computer, for example to produce video images on one or both monitors 14; mini C-arm x-ray systems embodying the invention may, of course, also or alternatively operate to provide other representations or manipulations of the data.

As thus far described, the system 10 is essentially similar to currently available mini C-arm x-ray fluoroscopic imaging systems such as those shown in the aforementioned allowed application and patent, to which reference may be made for further exemplification of details of structure and operation thereof. More particularly, in common with such systems the structure of the C-arm 20 includes a rigid C-shaped track 32 of hollow, rectangular cross-section, continuously curved along an arc of a circle, with opposed parallel planar longitudinal side surfaces 32a and 32b extending lengthwise, and two opposed ends 32c and 32d spaced apart by a gap and respectively carrying the x-ray source 22 and x-ray detector 24. A support member 34 slidably mounts the C-shaped track 32 for sliding rotary movement of the track, relative to the support member, along a circular path coincident with the arc of curvature of the track, so that the x-ray source and detector can be moved rotatably (orbited) together about an axis 36 coincident with the center of circular curvature of the C-arm track and perpendicular to the plane containing the arc of curvature of the track.

Figure 2:
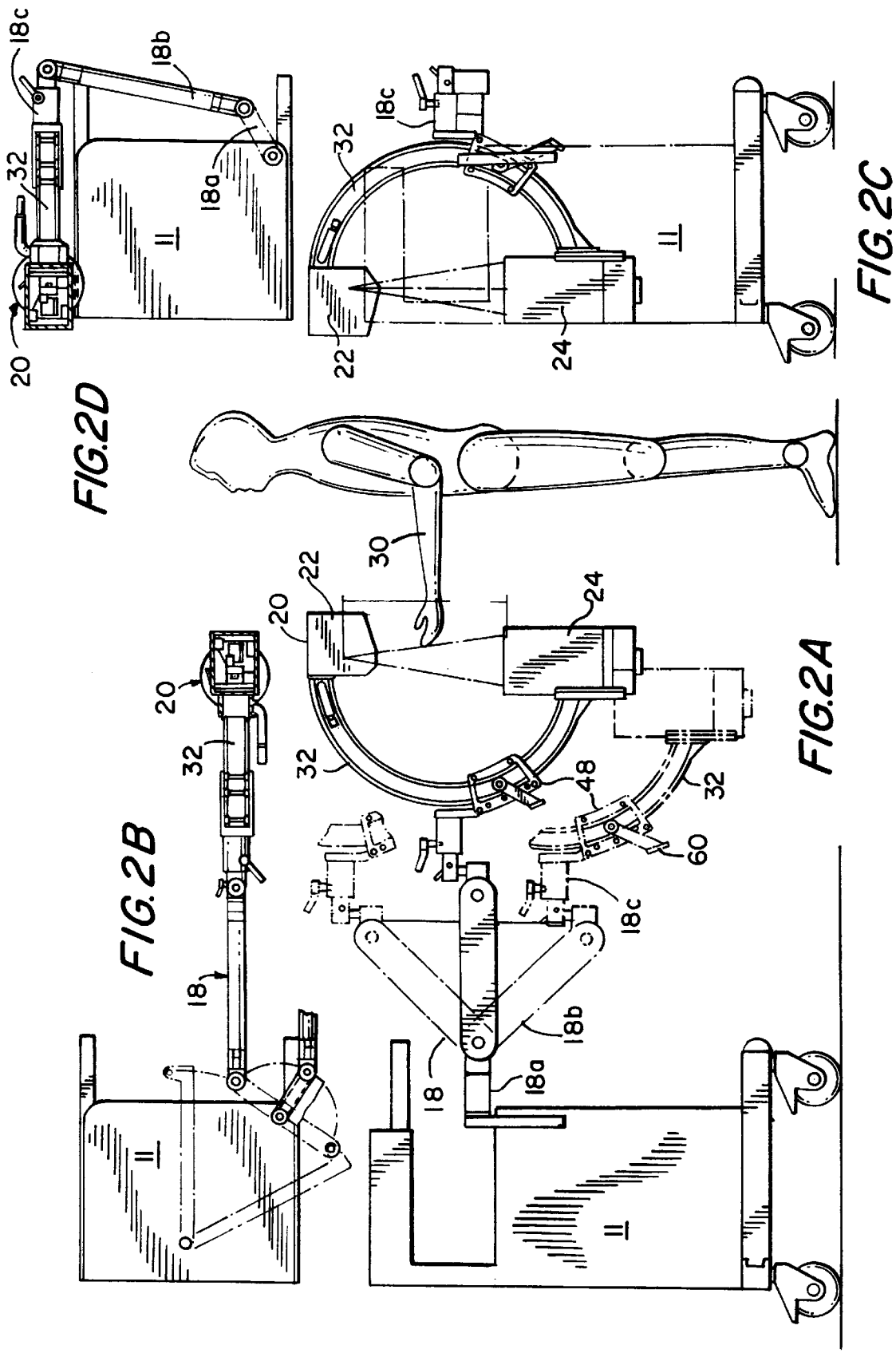
FIGS. 2A, 2B, 2C and 2D are reduced-scale views of the apparatus of FIG. 1, respectively in side elevation with the arm assembly extended (showing different positions thereof), in plan with the arm assembly extended, in side elevation with the arm assembly folded, and in plan with the arm assembly folded.
Figure 3:
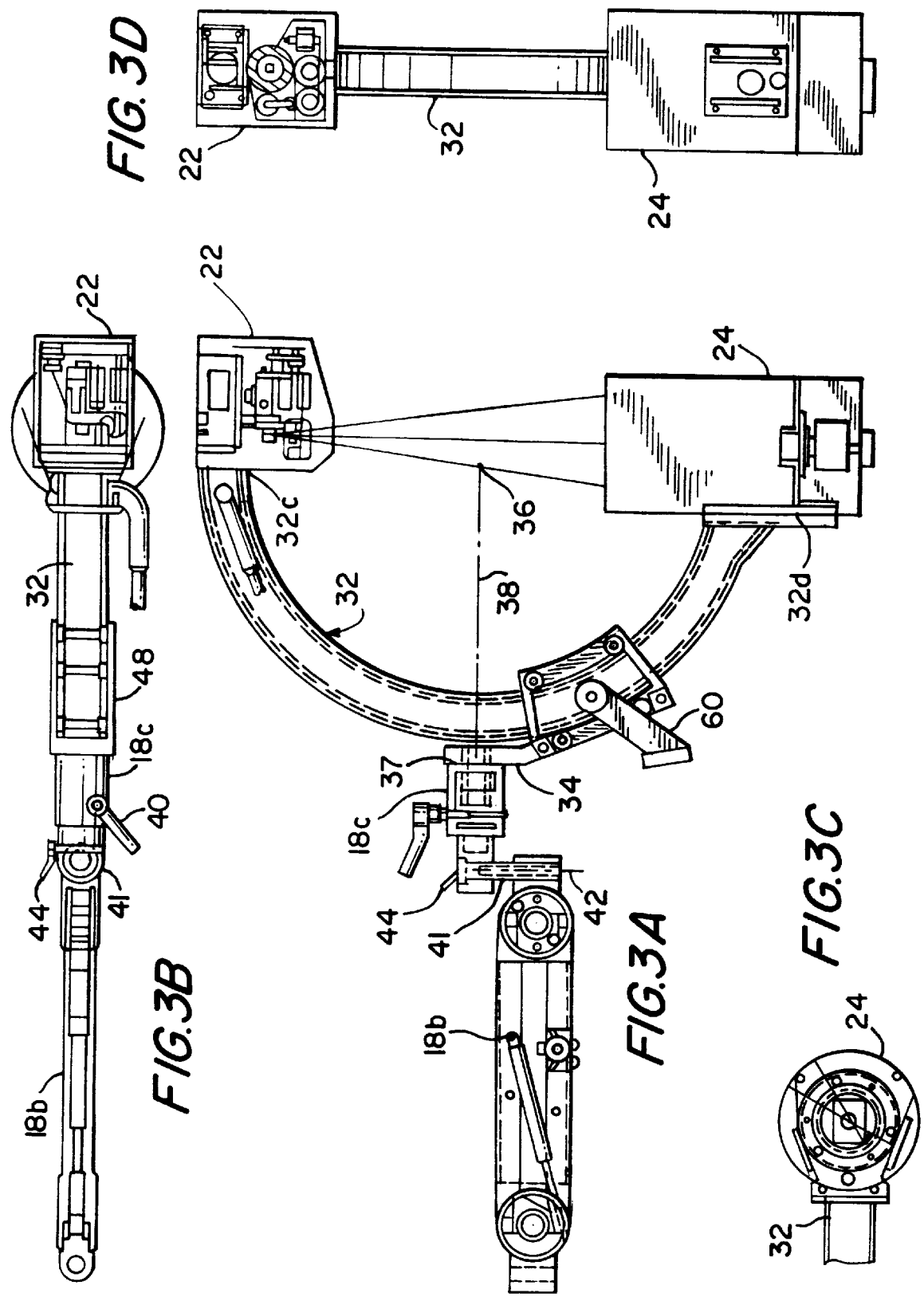
FIGS. 3A, 3B, 3C and 3D are enlarged views of a portion of FIG. 1, respectively in side elevation, top plan, fragmentary bottom plan, and front elevation.

The arm assembly 18, which comprises a succession of arms 18a, 18b and 18c, pivotally connected to each other end-to-end, has a proximal or inner end 18d pivotally connected to the wheeled cabinet 11 and a distal or outer end 18e. As best seen in FIG. 2A, this arm assembly permits vertical as well as pivotal positioning of the C-arm. The support member 34 is pivotally mounted on the distal end 18e of the arm assembly (i.e., on the distal end of arm 18c) as indicated at 37 for rotation, relative thereto, about a horizontal axis 38 perpendicular to the axis 36 of sliding rotation of the C-shaped track 32 relative to the support member. A locking mechanism 40 is provided on arm 18c to lock the pivotal mounting 37 in any desired angular position. Also, the arm 18c is pivotally secured at its proximal end, as indicated at 41, to the distal end of the arm 18b for rotary movement relative thereto about a vertical axis 42, and a locking mechanism 44 is provided for pivotal mounting 41.

Figure 4:
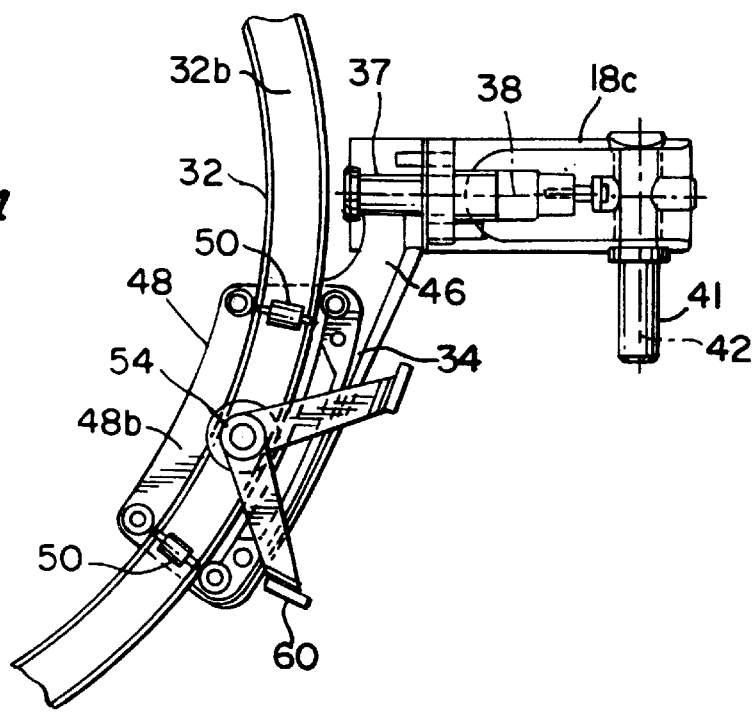
FIG. 4 is a further enlarged side elevational view of the supporting member and locking mechanism of the embodiment of FIG. 1, showing a fragmentary portion of the C-shaped track.

The support member 34 includes a cast metal body 46 (FIGS. 12A and B) that extends downwardly (as seen, e.g., in FIG. 4) from the pivotal mounting 37 with an outward curvature conforming to the curvature of the C-shaped track 32. Mounted on this body is a guide structure 48, elongated in the direction of the curved path of movement of the track 32 relative to the support member, and constituted of two generally planar side plates 48a (FIGS. 11A and B) and 48b secured together in parallel, spaced-apart relation to define, between them, a passage through which the C-shaped track extends, with its two longitudinal side surfaces 32a and 32b respectively facing the inner surfaces of the two side plates. Rollers 50 mounted within the guide structure engage the track 32 to provide smooth, guided sliding movement of the track along its arcuate track. As will be apparent, the support member 34 including the body 46 and guide structure 48 constitutes the mounting and support for the C-shaped track (bearing the x-ray source and detector at its opposite ends) in the mini C-arm system of FIG. 1.

Figure 5A:
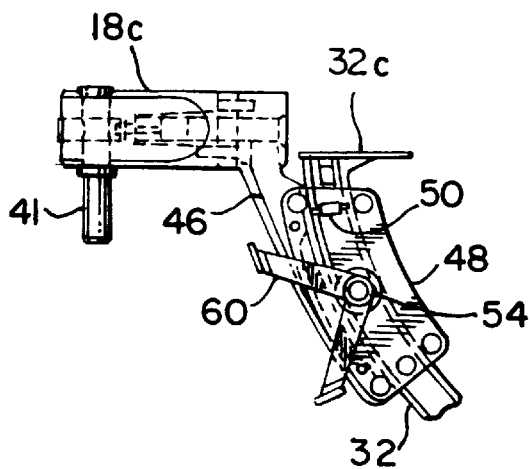
FIGS. 5A and 5B are views similar to FIG. 4 but somewhat reduced in scale and respectively showing the positions of the C-shaped track adjacent the lower and upper limits of its sliding movement relative to the supporting member.
Figure 5B:
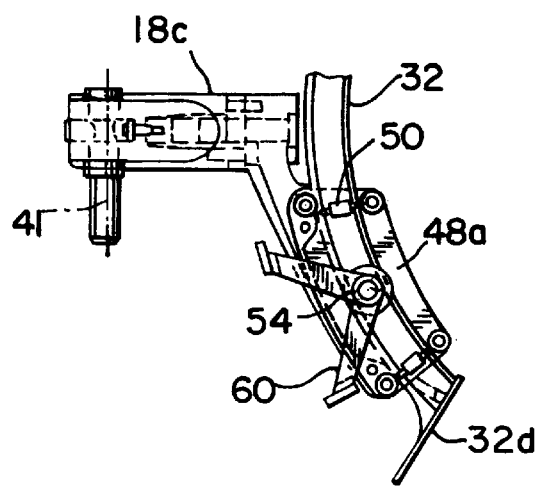

FIGS. 5A and B show the C-shaped track at its extreme lower and upper positions within its curved path of longitudinal (orbital) movement about axis 36. At the extreme lower position of the track, its upper end 32c (bearing the x-ray source, not shown in FIG. 5A) is closely adjacent the guide structure 48, being just above the guide structure in the view of FIG. 5A; at the extreme upper position of the track, its lower end 32d (bearing the detector, not shown in FIG. 5B) is closely adjacent the guide structure 48, being just below the guide structure in the view of FIG. 5B.

Figure 6:
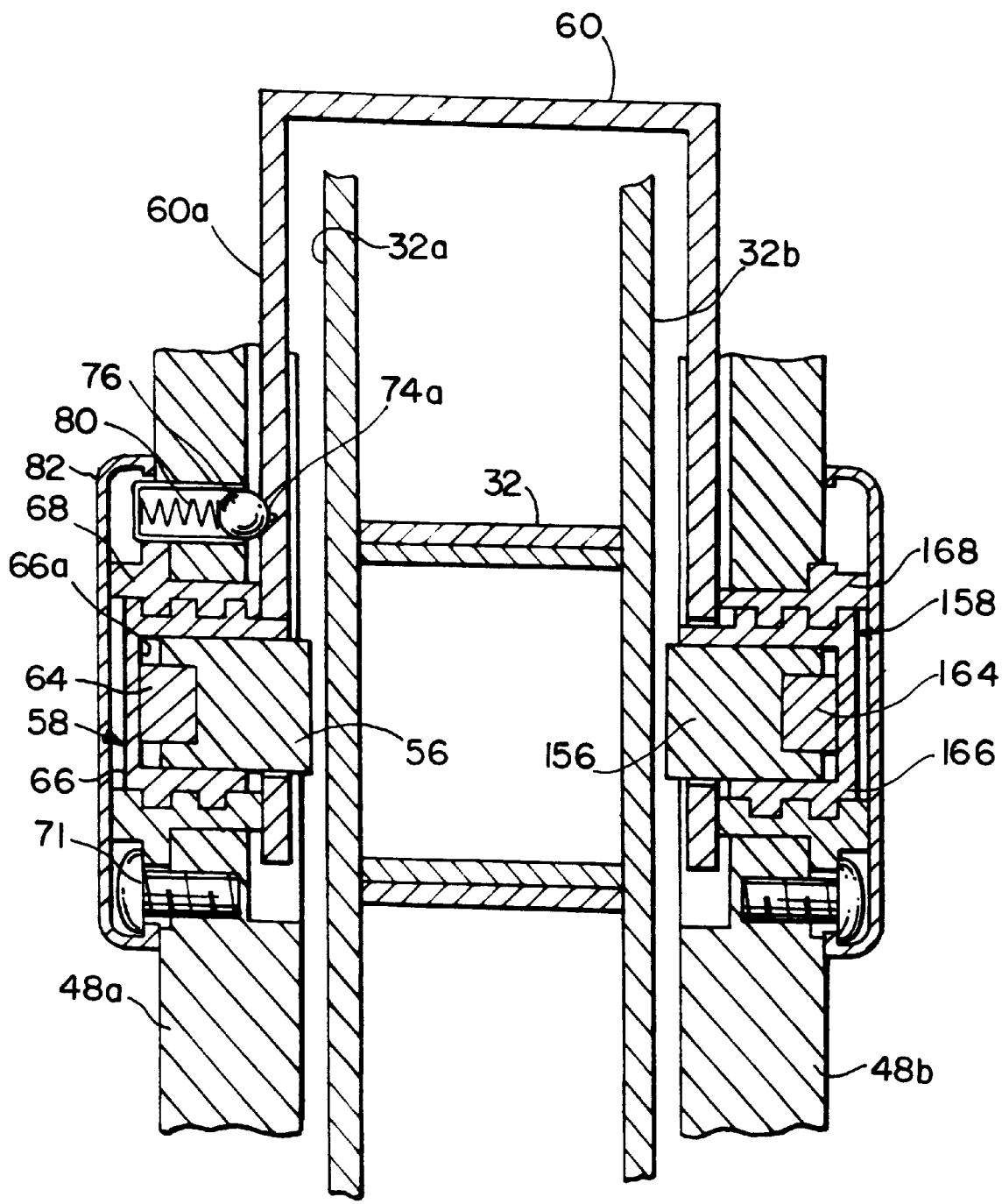
FIG. 6 is a still further enlarged, schematic sectional view of the locking mechanism and associated structures of the embodiment illustrated in FIG. 4.

The locking mechanism 54 of the present invention, in its illustrated embodiment, is carried on the guide structure 48 and serves to arrest the track 32, with any of a plurality of incrementally different degrees of drag, at any desired position in its arcuate path at or between the end points illustrated in FIGS. 5A and B. As best seen in FIG. 6, this locking mechanism broadly comprises a brake shoe 56 for bearing against the track surface 32a, and a driver 58, mounted in the side plate 48a of the guide structure 48 of the support member 54 and carrying the brake shoe 56, for moving the brake shoe toward and away from the track surface 32a through a range of positions between a first position in which the shoe bears against the track surface with full braking force to prevent movement of the track along the path and a second position in which the shoe exerts substantially no braking force on the surface. The shoe 56 is resiliently compressible, as hereinafter explained, toward the driver 58 so that as the shoe moves progressively through at least a substantial part of its aforesaid range of positions it exerts a progressively varying force on the track surface. Further, the locking mechanism includes a handle 60 connected to the driver 58 for operating the driver to move the shoe through its range of positions, and a detent 62 cooperating with the handle to releasably arrest the handle in each of a plurality of locations (five, in the illustrated embodiment, as indicated in FIG. 8) respectively corresponding to a like plurality of positions of the brake shoe, within the range of shoe positions, including the aforementioned first and second positions.

Resilient compressibility of the brake shoe is provided, in this embodiment, by a resilient bias-exerting device shown as a helical spring 64 (under compression) acting between the shoe 56 and the driver 58, the bias exerted by device 64 urging the shoe away from the driver to a limited extent such that when the shoe is in its aforementioned second position, the shoe does not engage the track surface 32a.

More specifically, the driver 58 comprises a screw 66 (FIGS. 10A and B) connected to the brake shoe 56 and a nut 68 (FIGS. 9A and B) carried by the side plate 48a of the guide structure of the support member 34, the screw being threaded in the nut whereby the screw and nut have a common thread axis. The handle 60 is connected to one of these two elements (screw and nut) for rotation therewith about the thread axis, and the other of the screw and nut is held against rotation about the thread axis. In the illustrated embodiment, the handle is connected to the screw 36 by a key engagement portion 70 (FIG. 8) so as to rotate with the screw while permitting limited axial movement of the screw (relative to the handle and the side plate 48a) along the thread axis, i.e., toward and away from the track surface 32a, while the nut 68 is fixedly anchored to the side plate 48a by a mounting screw 71, being thereby held against rotation relative to the side plate.

Figure 8:
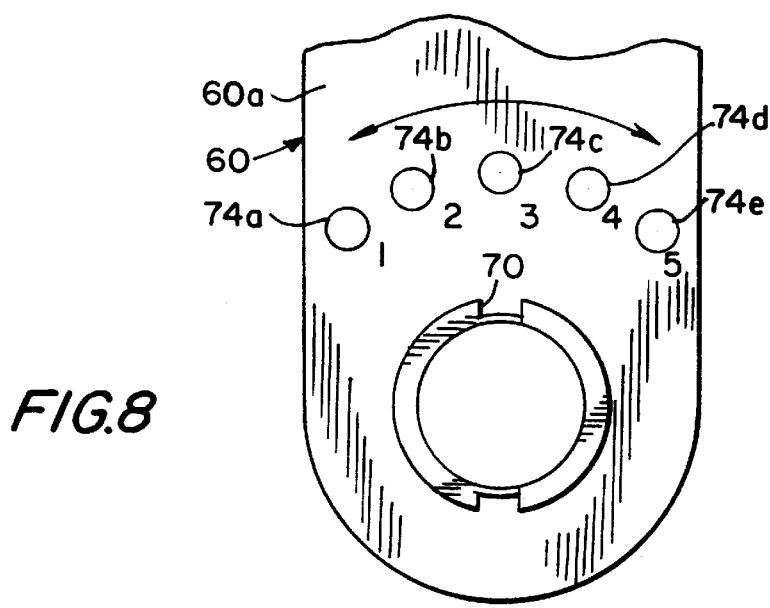
FIG. 8 is a fragmentary elevational view of the handle of the locking mechanism of the embodiment of FIG. 6.

Referring further to FIGS. 6 and 8, the handle 60 has a surface 60a, facing the side plate 48a, formed with a plurality of indentations 74a, 74b, 74c, 74d and 74e, corresponding in number to the plurality of locations at which the handle can be arrested by the detent, five such indentations (and locations) being provided in the embodiment shown. The detent 62 comprises a spring-loaded body having a convexly rounded surface, shown as a solid ball 76 urged toward the handle by a helical spring 80 under compression, mounted in the side plate 48a so as to be sequentially receivable in the indentations 74a . . . 74e to arrest the handle at each of the aforesaid plurality of locations, as the handle is rotated manually by the user about the thread axis of the driver screw and nut, turning the screw with it.

The screw 66 (FIGS. 10A and B) is formed with a central cylindrical recess 66a having a geometric axis and an open end facing the track surface 32a. The brake shoe 56 is received within this recess and is axially movable therein; it is at present preferred that the brake shoe 56 be a solid cylindrical body fabricated of urethane "70A."

The bias-exerting device, in the form of the resiliently compressible spring 64, is disposed within the recess 66a, acting between the screw 66 and the brake shoe 56, to urge the brake shoe toward the track surface 32a. For protection, a dished cylindrical cap 82 may be fitted over the exposed outer surface of the locking mechanism on the side plate 48a.

The elements of the locking mechanism thus far described are duplicated on the other side of the guide structure 48, as also seen in FIG. 6, so that braking forces are exerted simultaneously against the opposed side surfaces 32a and 32b of the track 32. Thus, the locking mechanism further includes a second brake shoe 156 (identical to shoe 56) for bearing against the second surface 32b of the track, and a second driver 158 (comprising a recess-defining screw 166 and nut 168, threaded oppositely to screw 66 and nut 68), mounted in the side plate 48b and carrying the second brake shoe, for moving the second brake shoe toward and away from the second track surface 32b through the aforesaid range of positions as the first brake shoe 56 is moved toward and away from the first track surface 32a. The second shoe 156 is made resiliently compressible toward the second driver by to the provision of a spring 164 within the recess of screw 166 and corresponding positionally and functionally to spring 64 described above) such that as the second shoe moves progressively through at least a substantial part of the range of shoe positions, it exerts a progressively varying force on the second track surface. The handle 60 is formed as a yoke or U-shaped member extending over but (throughout its angular range of movement) outwardly and thus clear of the path of movement of the track 32, being connected to the screw 166 of the second driver for operating the second driver to move the second brake shoe 156 toward and away from the track as the first shoe moves through its range of positions.

Figure 7:
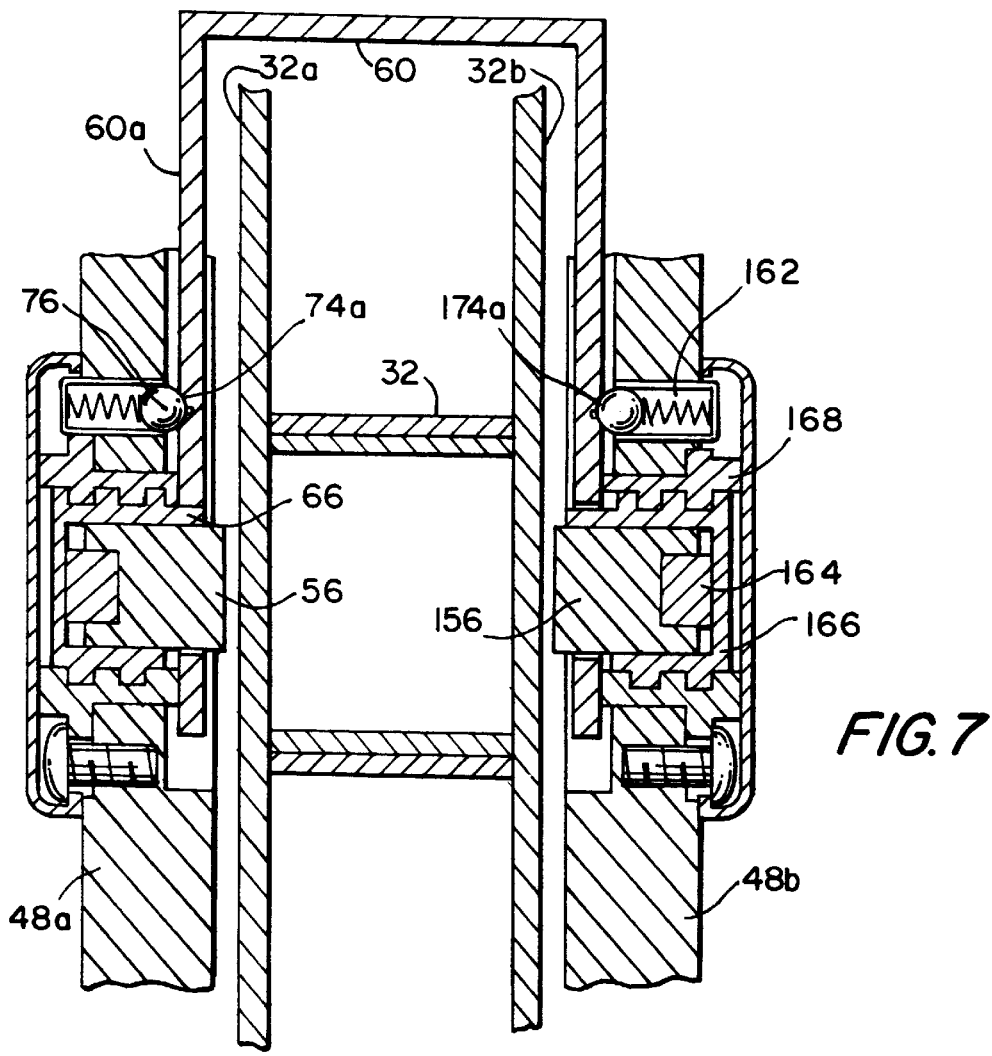
FIG. 7 is a view similar to FIG. 6 of a somewhat modified embodiment of the invention.

If desired, as shown in FIG. 7, a second detent 162 and a cooperating set of recesses 174a, etc., in the side of the handle adjacent side plate 48b, may be provided to enhance the security with which the handle is arrested at each of its five (or other predetermined number of) detent positions. One or both of the side plates 48a and 48b may have a V-shaped recess 48c (FIGS. 11A and B) formed in its inwardly-facing surface to define the range of movement of the handle 60 and to provide stop edges interferingly engaging the edge of the handle at its limits of travel.

The operation of the described locking mechanism may now be readily understood. In the array of five detent positions 74a, 74b, 74c, 74d and 74e shown in FIG. 8, position 74a is the fully-locked position at which maximum braking force is exerted by the shoes 56 and 156 against the track 32 to hold the track fixedly against sliding movement in either direction; position 74e at the other end of the array of detent recesses in the handle surface is the free position at which the brake shoes exert no force on the track and the track is free to slide in the guide structure; and positions 74b, 74c and 74d are intermediate brake positions (hard to soft) at which incrementally decreasing degrees of drag are exerted by the brake shoes on the track. The operator (e.g. the physician using the mini C-arm x-ray system) manually moves the handle to a desired one of these positions, for example to a light-braking position to tentatively hold the x-ray source and detector at a first chosen location in their orbital path while she or he evaluates that location, then pulls the C-arm along its track by manual force against the light drag for fine positional adjustment, and finally moves the handle to the fully locked position to secure the source and detector for use to examine a patient's extremity.

In these manipulations, turning of the handle 60 turns the screws 66 and 166 threaded within nuts 68 and 168 and, since the nuts are fixedly secured to the side plates 48a and 48b, causes the screws to move axially toward or away from the facing surfaces 32a, 32b of the C-shaped track 32 disposed between the shoes. Whether the shoes move toward or away from the track is determined by the direction in which the handle is turned, the two screws and their associated nuts on opposite sides of the track being oppositely threaded, as mentioned above, so that turning of the handle causes both screws either to converge toward or diverge away from the track.

Each time one of the handle indentations 74a . . . 74e comes into register with the detent ball 76 as the handle turns, the detent spring 80 urges the ball to seat in the indentation, arresting the handle. The shape and dimensions of the indentations and the force of the detent spring are such as to hold the handle stably in any such position but to be capable of being overcome by manual force exerted on the handle to rotate it, so that the operator can move the handle from one detent position to another.

If a second detent 162 and associated handle indentations 174a, etc., are provided as shown in FIG. 7, the retention of the handle at any detent position (i.e., any angular position corresponding to seating of the detent ball in one of the handle indentations) may be more evenly balanced, and increased in strength, while still enabling manual movement of the handle from one to another of the detent positions.

At the extreme limits of handle travel, respectively corresponding to indentations 74a and 74e, the screws 66 and 166 are at their limits of axial travel respectively toward and away from the facing surfaces 32a and 32b of the track 32, such range of axial travel being permitted by the design of the key engagement portions of the handle with the screws. When the detent ball 76 seats in indentation 74a and the screws are maximally extended toward the track 32, the springs 64 and 164 are under maximal compression and the two brake shoes 56 and 156 are pressed with maximum force against the opposed track surfaces to hold the track most securely against and displacement relative to the support member 34. Conversely, when the detent ball seats in indentation 74e, the screws are at their axial positions furthest away from the surfaces 32a and 32b of the track, and the springs 64 and 164 are under minimal compression; preferably, the elements of the guide structure and locking mechanism 54 are so arranged and disposed that, at this time, the brake shoes are out of contact with the track surfaces, so that the track is entirely free to slide along its arcuate track (relative to the support member) without drag or hindrance by the brake shoes.

At each intermediate detent position (i.e., at the positions respectively corresponding to seating of the detent ball in indentations 74b, 74c and 74d), the screws are close enough to the track so that the shoes engage the opposed track surfaces and the springs are under a degree of compression that provides sufficient drag to arrest the track against free sliding movement. The extent of such compression, and thus the degree of drag exerted, depends on how close the screws are to the track, and this distance (along the thread axis) differs incrementally from one intermediate detent position to the next, because the screws are incrementally closer to the track surfaces when the detent ball is at indentation 74d than when it is at indentation 74c, and are incrementally closer to the track surfaces when the detent ball is at indentation 74c than when it is at indentation 74b. Thus, the successive indentations in the handle represent incrementally increasing (or decreasing) degrees of drag to which the handle may be moved by the operator to apply, selectively and assuredly, a particular desired degree of drag at and particular phase of the C-arm positioning procedure. Between these manipulations, the detent arrangement is effective to retain the handle at the selected position (and thereby to prevent undesired release of the track) even if the handle is inadvertently subjected to the pulling force of a surgical drape.

It is to be understood that the invention is not limited to the procedures and embodiments hereinabove specifically set forth, but may be carried out in other ways without departure from its spirit.

What is claimed is:

1. In C-arm apparatus, in combination:
   (a) a rigid C-shaped track having a circular arc of curvature and opposed free ends, spaced apart by a gap, for respectively bearing two elements which are to be maintained in fixed relation to each other and to be adjustably positionable in relation to an object which is to be disposed in the gap, said track having a surface extending along its length;
   (b) a member supporting said track for longitudinal guided sliding movement along an arcuate path coincident with the arc of curvature of the track to orbit said elements;
   (c) a brake shoe for bearing against said track surface;
   (d) a driver, mounted in said supporting member and carrying said brake shoe, for moving said brake shoe toward and away from said track surface through a range of positions between a first position in which the shoe bears against the track surface with full braking force to prevent movement of the track along the path and a second position in which the shoe exerts substantially no braking force on the surface, said shoe being resiliently compressible toward said driver such that as the shoe moves progressively through at least a substantial part of said range it exerts a progressively varying force on the track surface;
   (e) a handle connected to the driver for operating the driver to move the shoe through said range of positions; and
   (f) a detent cooperating with said handle to releasably arrest said handle in each of a plurality, greater than two, of locations respectively corresponding to a like plurality of positions of said brake shoe, within said range, including said first and second positions.

2. C-arm apparatus as defined in claim 1, including a resilient bias-exerting device acting between said shoe and said driver such that said shoe is resiliently compressible toward said driver as aforesaid, the bias exerted by said device urging the shoe away from the driver to a limited extent such that when said shoe is in the second position, the shoe does not engage the track surface.

3. C-arm apparatus as defined in claim 1, wherein said driver comprises a screw connected to said brake shoe and a nut carried by said supporting member, said screw being threaded in said nut whereby said screw and nut have a common thread axis, said handle being connected to one of said screw and nut for rotation therewith about said thread axis, and the other of said screw and nut being held against rotation about said thread axis.

4. C-arm apparatus as defined in claim 3, wherein said handle has a surface, facing a portion of said supporting member, formed with a plurality of indentations corresponding in number to said plurality of locations, and wherein said detent comprises a spring-loaded body having a convexly curved surface, mounted in said portion of said supporting member so as to be sequentially receivable in said indentations to arrest said handle at each of said plurality of locations.

5. C-arm apparatus as defined in claim 3, wherein said handle is connected to said screw for rotation therewith.

6. C-arm apparatus as defined in claim 3, wherein said screw is formed with a central cylindrical recess having a geometric axis and an open end facing said track surface, wherein said brake shoe is received within said recess and is axially movable therein, and further including a resiliently compressible spring, disposed within said recess and acting between said screw and said brake shoe, urging said brake shoe toward said track surface.

7. C-arm apparatus as defined in claim 1, wherein said track has a second surface extending along its length and opposed to the first-mentioned surface, and including a second brake shoe for bearing against said second surface, and a second driver, mounted in said supporting member and carrying said second brake shoe, for moving said second brake shoe toward and away from said second track surface through said range of positions, said second shoe being resiliently compressible toward said second driver such that as the second shoe moves progressively through at least a substantial part of said range it exerts a progressively varying force on the second track surface, said handle being connected to the second driver for operating the second driver to move the second brake shoe through said range of positions as said first shoe moves through said range of positions, said first and second shoes cooperating to exert braking force simultaneously against both said first-mentioned surface and said second surface of said track.

8. C-arm apparatus as defined in claim 1, wherein said two elements are, respectively, an x-ray source and an x-ray detector that face each other across the gap so that x-rays emitted by the source are incident on and detected by the detector, the source and detector being so arranged that when an object such as a human extremity is interposed in the gap and irradiated with x-rays from the source, the detector produces data representative of characteristics of the interposed object.

9. C-arm apparatus as defined in claim 8, comprising a mini C-arm fluoroscopic imaging system, and further including an arm assembly having a proximal end and a distal end, the supporting member being pivotally mounted on said distal end for rotation relative thereto, about a first axis; and a base to which the proximal end of the arm assembly is pivotally mounted for rotation about a second axis different from said first axis.

\* \* \* \* \*